(12) United States Patent
Harichian et al.

(10) Patent No.: US 6,623,728 B2
(45) Date of Patent: Sep. 23, 2003

(54) COSMETIC SKIN CARE COMPOSITIONS AND CONTAINING GUM MASTIC

(75) Inventors: Bijan Steven Harichian, Warren, NJ (US); John Steven Bajor, Ramsey, NJ (US); Laura Rose Palanker, Salt Lake City, UT (US)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 89 days.

(21) Appl. No.: 09/872,925

(22) Filed: Jun. 1, 2001

(65) Prior Publication Data

US 2002/0018757 A1 Feb. 14, 2002

Related U.S. Application Data

(60) Provisional application No. 60/215,267, filed on Jun. 30, 2000.

(51) Int. Cl.[7] ................................................ A61K 31/74
(52) U.S. Cl. ................. 424/78.03; 424/401; 424/78.02; 514/844; 514/847; 514/938
(58) Field of Search .............................. 424/59, 60, 401, 424/70.11, 74, 70.1, 78.02, 78.03; 847/938

(56) References Cited

U.S. PATENT DOCUMENTS

| | | | |
|---|---|---|---|
| 5,422,100 A | 6/1995 | Eliaz et al. | 424/70 |
| 5,637,290 A | 6/1997 | Sodis et al. | 424/49 |
| 5,690,948 A | 11/1997 | McCook et al. | 424/401 |
| 6,203,782 B1 * | 3/2001 | Eliaz et al. | 424/70.1 |

FOREIGN PATENT DOCUMENTS

WO 91/10196 7/1991

OTHER PUBLICATIONS

Triterpenoids From Gum Mastic, The Resin of Pistacia Lentiscus, *Phytochemistry*, vol. 30, No. 11, pp. 3709–3712, 1991.

*Cosmetics Science and Technology*, pp. 46–47, vol. 1, Krieger Publishing Co., 1992.

* cited by examiner

*Primary Examiner*—Jose' G. Dees
*Assistant Examiner*—Sharmila S Gollamudi
(74) *Attorney, Agent, or Firm*—Ellen Plotkin

(57) ABSTRACT

Cosmetic skin care methods comprising applying to the skin compositions containing gum mastic. The inventive compositions provide control of sebum secretion from sebocytes, improved oil control and improved skin feel, prevent shine and stickiness, while also providing anti-aging benefits which results in reduced appearance of wrinkles and aged skin, improved skin color, treatment of photoaged skin, improvement in skin's radiance and clarity and finish, and an overall healthy and youthful appearance of the skin.

6 Claims, No Drawings

COSMETIC SKIN CARE COMPOSITIONS AND CONTAINING GUM MASTIC

This application claims priority to provisional application No. 60/215,267 filed on Jun. 30, 2000.

FIELD OF THE INVENTION

Cosmetic skin care methods and compositions for conditioning human skin by topical application of cosmetic compositions containing gum mastic.

BACKGROUND OF THE INVENTION

Sebum is skin oil which is produced by sebocytes (cells of the sebaceous glands in the skin) and is then secreted to the skin surface. A frequent, undesirable skin condition is "oily skin," the condition which results from the excessive amount of sebum on the skin. Oily skin is associated with a shiny, undesirable appearance and a disagreeable tactile sensation and affects various age groups. Cosmetic products which can condition the skin to provide sebum control is therefore highly desirable.

In recent years, consumer demand for "natural" products has led to the use of plant extracts in various skin care compositions. The prior art discloses gum/resins and oils from plants for various uses. For example, WO 91/10196 assigned to Parfums Christian Dior (hereinafter "Dior '196"), discloses the use of forms of the resin guggul, an extract from a plant of the genus Commiphora, originating in India. Dior '196 discloses the use of guggul as a cosmetic agent for improving the appearance of the skin surface and in particular, for reducing the depth of wrinkles and making fine lines disappear.

U.S. Pat. No. 5,690,948 issued to McCook et al. (hereinafter "McCook '948"), discloses the use of ethyl acetate extracts of the gum/resin guggal, referred to as gugulipid. McCook '948 discloses the use of gugulipid and alcoholic fractions thereof in antisebum and antioxidant compositions.

Gum mastic, which may be obtained as a trunk exudate of the species *Pistacia lentiscus* L., an evergreen shrub of the Anacardiaceae family, has been produced since ancient times on the island of Chios, Greece. Components of gum mastic include α-pinene, camphene, β-pinene, sabinene, myrcene, δ-3-carene, limonene, eucalyptol, Yy-terpinene, p-cymene, terpinolene, terpinene-1-ol-4 and α-terpineol. See *Fragrance Raw Materials Monographs*, Mastic Absolute. Certain terpenoids of gum mastic have also been identified and isolated. See "Triterpenoids From Gum Mastic, The Resin of Pistacia Lentiscus," *Phytochemistry*, Vol. 30, No. 11, pp. 3709–3712, 1991.

U.S. Pat. No. 5,422,100 issued to Eliaz et al. (hereinafter "Eliaz '100"), discloses the use of gum mastic as a carrier for hair and skin conditioning methods and products. In particular, Eliaz '100 teaches topical application of a treatment agent to the skin for promoting hair growth, preventing, stopping or minimizing hair loss, conditioning the hair and scalp, thickening the hair, treating dandruff, smoothing skin, treating seborrheic dermatitis, treating psoriasis and like condition, and possibly including uses such as the healing of wounds in the skin. The gum mastic carrier provides a medium for the treatment agent with a capability for penetrating into the skin and/or hair follicles.

U.S. Pat. No. 5,637,290 issued to Sodis et al., discloses the use of natural mastic from chios, extract mastic oil, or synthetic mastic agents for production of toothpaste, mouthwash, mouth deodorizers, suntan lotions, hair products, and cosmetics.

Practically all penetration and absorption into the skin occurs via the hair follicles and the sebaceous glands. *Cosmetics Science and Technology*, pp. 46–47, vol. 1, Krieger Publishing Co., 1992. Therefore, an ideal cosmetically beneficial composition for delivery of an active to the skin delivers the active such that it adheres to skin or hair. It is well known in the art to use emulsions because of their ability to deliver both oil and water to the skin and hair. Conventionally, actives have been delivered in water-in-oil or oil-in-water emulsions, with oil-in-water emulsions being preferred because of the desirable aesthetic and elegant properties such as rich and creamy, yet non-greasy skin feel. Id. at 47.

The prior art discussed above does not disclose cosmetic mediums that provide enhanced delivery of plant extracts to the skin for a dual benefit of sebum suppression and anti-aging benefits. Therefore, a need remains for such cosmetic products containing cost-effective and readily available natural ingredients.

SUMMARY OF THE INVENTION

The present invention includes an oil-in-water cosmetic skin care emulsion composition comprising:

(a) from about 0.001 wt. % to about 10 wt. % of solubilized gum mastic (b) a volatile, water miscible solvent; and (c) a cosmetically acceptable vehicle.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

The term "skin" as used herein includes the skin on the face, neck, chest, back, arms, hands, legs, and scalp.

The term "gum mastic" as used herein means the resin from the species *Pistacia lentiscus* L., an evergreen shrub of the Anacardiaceae family, found on the island of Chios, Greece.

The term "solubilized" as used herein means that at least 90% of gum mastic present in the final composition is solubilized.

The term "water miscible" as used herein means that at least 95% of solvent present in the final composition is miscible in water.

According to the present invention, solubilized gum mastic controls sebum secretion and/or controls oily skin and prevents skin wrinkles and laxity.

All amounts are by weight of an oil-in-water emulsion, unless otherwise indicated.

Sebum is oil produced by sebocyte cells of the sebaceous glands. Inhibition of sebocyte lipogenesis reduces excretion of sebum, thereby reducing and/or controlling oily skin. Alternatively, enhancing collagen production aids in preventing skin wrinkles and laxity. It has been found as part of the present invention that solubilized gum mastic unexpectedly possesses sebum suppression activity through inhibition of sebocyte lipogenesis as well as providing anti-aging benefits through enhanced collagen production.

Gum mastic in crystal form may be obtained from Sigma Chemicals or Spectrum. Premixed solutions of gum mastic (e.g. Lentisque Absolute) may be obtained from Biolandes Parfums. Relative to extracts such as gugulipid, gum mastic is inexpensive and therefore cost-effective in use in cosmetic skin care compositions.

Gum mastic is oil soluble and is therefore dissolved in a suitable solvent in the inventive compositions. In the preferred embodiment, volatile water miscible solvents are used because such solvents evaporate after application to the skin. The gum mastic in the inventive compositions therefore remains in contact with the skin even after evaporation of the solvent until the gum mastic penetrates into the skin and hair follicles, providing both suppression of sebum and anti-aging benefits. In contrast, non-volatile, water immiscible solvents such as isopropyl myristate as disclosed in Eliaz '100, do not evaporate. Therefore, even after application onto the skin, the gum mastic would remain trapped in the solvent such that only a final diluted amount of gum mastic would penetrate the hair follicles.

Suitable volatile, water miscible solvents include ethanol, methanol, propanol, isopropyl alcohol and mixtures thereof. Ethanol is preferred due to commercial availability. To realize a cosmetic benefit, the ratio of gum mastic to solvent can vary from 1:75, preferably from 1:50, and most preferably from 2:1.

Solubilized gum mastic is present in the inventive compositions between 0.001 to 10% by weight of the composition, preferably from 0.01 to 1%, and most preferably from 0.01 to 0.05%.

Although other forms are contemplated to be within the scope of the invention, the inventive composition is preferably an oil-in-water emulsion because the continuous phase is aqueous, creating a less greasy feel on the skin. It is well known in the art that actives in the larger, continuous aqueous phase of an oil-in-water emulsion have an increased probability of reaching the targeted tissues in the skin since the aqueous phase is in direct contact with the skin immediately upon application. See generally, *Cosmetics Science and Technology* at 47. In contrast, actives in the oil phase of an oil-in-water emulsion must first penetrate into the water phase and then into the skin. Therefore, the solubilized gum mastic is present in the aqueous phase of the inventive composition.

It is also well known in the art that oil solubility of an active enhances penetration of the active into the skin by virtue of mutual miscibility with the sebum present in the hair follicles and sebaceous glands. *Cosmetics Science and Technology* at 47. Solubilized gum mastic is soluble in oil. Thus, in the inventive compositions, the solubilized gum mastic is dissolved in a volatile, water miscible solvent such as ethanol, thereby remaining present in the continuous aqueous phase of the emulsion for immediate contact with the skin upon application. The volatile, water miscible solvents evaporate after application onto the skin, leaving the gum mastic supersaturated in the water phase of the emulsion. Supersaturation allows the gum mastic to remain in contact with the skin until penetration despite evaporation of the water phase after application.

The emulsion preferably contains at least 80 wt. % water, by weight of the vehicle. Preferably, the amount of water is at least 50 wt. % of the inventive composition, and most preferably from 60 to 80 wt. %, by weight of the composition.

Cosmetically Acceptable Vehicle:

The compositions according to the invention also comprise a cosmetically acceptable vehicle to act as a diluent, dispersant, or carrier for gum mastic in the composition, so as to facilitate its distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 40 to 90%, optimally between 60 and 90% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 and 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicone atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of active ingredients may be present in cosmetic compositions of the present invention. Actives are defined as skin benefit agents other than emollients and or ingredients that merely improve the physical characteristics of the composition. Although not limited to this category, general examples include anti-acne agents, additional anti-sebum agents, and sunscreens.

Anti-acne agents include but are not limited to benzoyl peroxide (up to 20 wt. % may be included), retinoids (typically 0.025%–0.05%), salicylic acid (typically up to 2 wt. %), and sulphur (up to 8 wt. %).

Retinoids increase collagen synthesis by dermal fibroblasts. This results in protection from sun damage and smoothening of wrinkled skin. The term "retinoids" as used herein includes retinoic acid, retinol, retinal, and retinyl esters. Included in the term "retinoic acid" are 13-cis retinoic acid and all-trans retinoic acid.

The term "retinol" as used herein includes the following isomers of retinol: all-trans-retinol, 13-cis-retinol, 11-cis-retinol, 9-cis-retinol, 3, 4-didehydro-retinol. Preferred isomers are all-trans-retinol, 13-cis-retinol, 3,4-didehydro-retinol, 9-cis-retinol, 9-cis-retinol. Most preferred is all-trans-retinol, due to its wide commercial activity.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecandate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate, retinyl lactate, retinyl glycolate, retinyl hydroxy caprylate, retinyl hydroxy laurate, retinyl tartarate.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX® and Benzophenone-3®, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Powders may be incorporated into the cosmetic composition of the invention to aid in oil control. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor ingredients may range anywhere from 0.001% up to 20% by weight of the composition.

Use of the Composition:

The composition according to the invention is intended primarily as a product for topical application to human skin, especially as an agent for controlling or preventing oily skin, for improving skin's radiance and clarity and finish, and for preventing or reducing the appearance of wrinkled, dry, aged or photoaged skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging:

The cosmetic skin composition of the invention can be in any form, e.g. formulated as a toner, gel, powder, mask, solid bar, adhesive patch, mousse, nonwoven or woven substrate (wipe), lotion, a fluid cream, or a cream.

The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

EXAMPLE 1

This example provided data on inhibition of sebocyte lipogenesis.

Secondary cultures of human sebocytes obtained from an adult male were grown in 48-well tissue culture plates (Costar Corp.; Cambridge, Mass.) until confluent. Sebocyte growth medium consisted of Clonetics Keratinocyte Basal Medium (KBM) supplemented with 14 $\mu$g/ml bovine pituitary extract, 0.4 $\mu$g/ml hydrocortisone, 5 $\mu$g/ml insulin, 10 ng/ml epidermal growth factor, $1.2 \times 10^{-10}$ M cholera toxin, 100 units/ml penicillin, and 100 $\mu$g/ml streptomycin. All cultures were incubated at 37° C. in the presence of 7.5% $CO_2$. Medium was changed three times per week.

On the day of experimentation, the growth medium was removed and the sebocytes washed three times with sterile Dulbecco's Modified Eagle Medium (DMEM; phenol red free). Fresh DMEM was added to each sample (triplicates) with 5 $\mu$L of gum mastic solubilized in ethanol. Controls consisted of addition of ethanol alone to phenol red. Each plate was returned to the incubator for 20 hours followed by the addition of $^{14}$C-acetate buffer (5 mM final concentration, 56 mCi/mmol specific activity). Sebocytes were returned to the incubator for 4 hours after which each culture was rinsed three times with phosphate buffered saline to remove unbound label. Radioactive label remaining in the sebocytes was harvested and counted using a Beckman scintillation counter.

Gum mastic solubilized in ethanol solvent ("gum mastic") as well as commercially obtained solutions of gum mastic in 50% propylene glycol ("Lentisque Absolute") were tested in the concentrations listed in Table 1 below.

Controls consisted of ethanol alone and phenol red, which has estrogen-like activity. Statistical significance was calculated using the student's T-test. The results are summarized in Table 1 below.

TABLE 1

| Treatment | % Reduction | T-test |
| --- | --- | --- |
| 0.00035% Phenol Red | 29.1 | 0.0055 |
| 0.0001% Lentisque Absolute | 44.3 | 0.015 |
| 0.001% Lentisque Absolute | 58.7 | $6.5 \times 10^{-7}$ |
| 0.01% Lentisque Absolute | 97.8 | $6.7 \times 10^{-9}$ |
| 0.0001% Gum Mastic | 44.3 | $1.0 \times 10^{-5}$ |
| 0.001% Gum Mastic | 94.0 | $7.0 \times 10^{-6}$ |

As shown in Table 1, solubilized gum mastic improved inhibition of sebocyte lipogenesis.

EXAMPLE 2

This example measured production of procollagen I by fibroblasts in response to treatment with gum mastic in solvent solutions, as well as control solutions.

Gum mastic solubilized in ethanol solvent ("gum mastic"), and obtained from Sigma were tested.

Collagen is a predominant skin protein. Its synthesis decreases with aging or photodamage. The degradation or destruction of collagen increases the tensile strength of the skin causing wrinkles and laxity. Many studies involving human subjects have shown that collagen type I is decreased with increasing severity of photodamage (See Kligman, A., JAMA, (1969), 210, pp. 2377–2380; Lavker, R., J. Inv Derm., (1979), 73, 79–66; Smith J. et al., J. Inv. Derm., (1962), 39, pp. 347–350; and Shuster, S. et al., Br. J. Dermatol., (1975), 93, pp. 639–643); and some correlation in the histology of wrinkles and reduction in collagen levels in the sun-exposed skin has been reported. See Chen, S.; Kiss, I., J. Inv. Derm., (1992), 98. pp. 248–254. Voorhees and colleagues have supported these findings by showing the restoration of collagen type I in photo-damaged human skin by a topical treatment with tretinoin. See Christopher, E., et al., The New Eng. Jou. of Medicine (1993), 329, pp. 530–535. Procollagen I is a precursor of collagen. Increased production of procollagen I in response to a test compound application is a marker of an increased collagen level.

Procollagen I Staining Protocol for Slot Blot

Neonatal human dermal fibroblasts were purchased from Clonetics Corp., San Diego, Calif. All materials for cell culture were purchased from Life Technologies, NY and used in passages 5–10. Cells were seeded at a density of approximately 7,500/well in the inner 48 wells of a 96-well plate in a medium containing DMEM (Dulbecco's Modified Eagle's Medium), high-glucose supplemented with 2 mM L-glutamine, 10% fetal bovine serum, and antibiotic and antimycotic solutions). Cells were then grown to confluence for 2 days. At confluence, the medium was removed and cells were washed with serum-free DMEM, and each well dosed with 200 $\mu$l of a solution of gum mastic in serum-free DMEM. Each dosing was replicated in the total of six wells. Gum mastic was used at concentrations indicated in Table 1 below. Control did not contain gum mastic. After 24 hours, the gum mastic/control solution was removed and cells were redosed with 100 $\mu$l of a solution of gum mastic in serum-free DMEM. After 24 hours, the gum mastic/control solution was again removed and stored over the weekend at 4° C.

with protease inhibitor (Aprotinin from Sigma) in a ratio of aprotinin to water of 1:200. The gum mastic was then diluted in DMEM (approximately 20 μl sample in 200 μl DMEM).

Nitrocellulose membrane and 3 sheets of filter paper were soaked in TRIS buffered saline (TBS, pH 7.3.). BioRad slot blot apparatus (BioRad Labs, CA) was set up with filter paper on bottom, membrane on top, and tightened. 100 ml TBS was added per well. Vacuum was used to suck wells through membrane. The diluted gum mastic/control solution was vortexed, then 100 μl was loaded per well and gravity dried. Procollagen from the gum mastic was bound to the membrane at this point in the procedure. Membrane was removed from the apparatus, excess cut off, and bottom right corner notched for orientation. The membrane was placed in blocking solution (5% milk powder in Dulbecco's phosphate buffered saline) overnight at 4° C., with shaking. The membrane was then again incubated for 1.5 hrs at room temperature with 1.5 mL Rat Anti-Human Procollagen Amino-Terminal Ab (Chemicon MAB1912) in TBS with 0.1% BSA (ratio of antibody to buffer/BSA was 1:100) in a sealed bag with shaking. The membrane was then removed; washed 3 times for 5 minutes in TBS/0.1% Tween. The membrane was then incubated for 1 hour at room temperature in 2 mL of Biotinylated Anti-Rat Peroxidase-Conjugated Ab (Vector Labs) in TBS with 0.1% BSA (ratio of antibody to buffer/BSA was 1:1000) in a sealed bag with shaking.

The membrane was again washed 3 times for 5 minutes in TBS/0.1%Tween. 3 mL PBS was incubated with 30 μl each of the working solutions from Vectastain Kit (Vector Laboratories) for 30 minutes. The membrane was placed in the resulting solution for 30 minutes in a sealed bag with shaking. The membrane was then removed and washed twice for 5 minutes in TBS/0.1%Tween. The membrane was then stained using the following solution:

12.5 mg 3-amino 9-ethyl carbazole (Sigma)

3.125 mL DMF (N,N-dimethylformamide, from Sigma)

21.5 mL 0.2M NaOAc buffer, pH 5.2

12.5 μl $H_2O_2$

The membrane was stained until color developed and the reaction stopped with 2 washes for 10 minutes in tap water. A transparency of the blot was prepared using a color copier. Blot was scanned on Bio-Rad GS-700 Image Analysis densitometer and volume (OD*mm$^2$) of color/slot determined using molecular analysis software. Fold increase was calculated as a ratio of densitometer reading for cells treated with a gum mastic concentration over control.

The results obtained for effects on collagen production are summarized in Table 2 below. The results obtained for effects on glycosaminoglycan synthesis are summarized in Table 3 below.

TABLE 2

| Test Compound (0.01%) | Average OD Reading | Standard Deviation | p-value (vs. control) | Fold increase over control |
|---|---|---|---|---|
| Control | 5400.5 | 610.0 | — | — |
| TGF-b | 7499.8 | 1023.0 | 0.011 | 1.4 |
| 0.005% Gum Mastic | 5984.0 | 849.4 | 0.036 | 1.1 |
| 0.05% Gum Mastic | 6008.0 | 468.7 | 0.0011 | 1.1 |

*TGF-b was incorporated as a positive control

As shown in Table 2, solubilized gum mastic increased collagen production.

TABLE 3

| Test Compound | Average OD Reading | Standard Deviation | p-value (vs. control) | Fold increase over control |
|---|---|---|---|---|
| Control | 4531.8 | 290.8 | — | — |
| TGF-b | 6382.3 | 409.5 | 4.0 ×10$^{-6}$ | 1.4 |
| 0.005% Gum Mastic | 5594.7 | 522.2 | 1.4 ×10$^{-4}$ | 1.2 |
| 0.05% Gum Mastic | 4952.8 | 377.7 | 0.056 | 1.1 |
| 0.5% Gum Mastic | 5463.3 | 206.5 | 7.9 ×10$^{-5}$ | 1.2 |

*TGF-b was incorporated as a positive control

As shown in Table 3, solubilized gum mastic enhanced glycosaminoglycan synthesis.

EXAMPLE 3

Example 3 illustrates topical compositions according to the present invention. The compositions can be processed in conventional manner. They are suitable for cosmetic use. In particular the compositions are suitable for application to oily skin or wrinkled, rough, flaky, aged and/or UV-damaged skin and/or dry skin and post-menopausal skin to improve the appearance and the feel thereof as well as for application to healthy skin to prevent or retard deterioration thereof.

| INGREDIENT | % w/w |
|---|---|
| OIL-IN-WATER EMULSION | |
| DI Water | 73.40 |
| Carbomer | 0.30 |
| Disodium EDTA | 0.10 |
| Glycerin | 3.00 |
| Polysorbate 20 | 2.50 |
| Butylene Glycol | 2.00 |
| Methylparaben | 0.30 |
| Triethanolamine 99% | 0.30 |
| Gum Mastic | 2.00 |
| Isopropyl Myristate | 5.00 |
| Octyl Palmitate | 3.00 |
| Cetyl Alcohol | 1.00 |
| Dimethicone, 100 cst | 0.50 |
| Beeswax | 0.30 |
| Propylparaben | 0.10 |
| Germall II | 0.10 |
| Fragrance | 0.10 |
| Total → | 10.00 |
| DI Water | 71.20 |
| Xanthan Gum | 0.20 |
| Disodium EDTA | 0.10 |
| Glycerin | 5.00 |
| Butylene Glycol | 2.00 |
| Methylparaben | 0.30 |
| Gum Mastic | 2.00 |
| Isopropyl Myristate | 5.00 |
| Octyl Palmitate | 3.00 |
| Cetyl Alcohol | 1.00 |
| Dimethicone, 100 cst | 0.50 |
| Steareth-2 | 0.40 |
| Steareth-2 1 | 3.00 |
| Propylparaben | 0.10 |
| Germall II | 0.10 |
| Fragrance | 0.10 |
| Total → | 100.00 |
| WATER-IN-OIL EMULSION | |
| DI Water | 63.30 |
| Disodium EDTA | 0.10 |

-continued

| INGREDIENT | % w/w |
|---|---|
| Glycerin | 3.00 |
| Propylene Glycol | 2.00 |
| Sodium Chloride | 0.70 |
| Methylparaben | 0.30 |
| Cyclomethicone | 14.00 |
| Gum Mastic | 2.00 |
| Isopropyl Myristate | 5.00 |
| Octyl Palmitate | 3.00 |
| Dimethicone Copolyol | 2.50 |
| Dimethicone, 100 cst | 0.50 |
| Beeswax | 0.30 |
| Propylparaben | 0.10 |
| Germall II | 0.10 |
| Fragrance | 0.10 |
| Total → | 100.00 |

HYDRO-GEL

| INGREDIENT | % w/w |
|---|---|
| DI Water | 81.85 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Gum Mastic | 2.00 |
| Ascorbic acid | 1.00 |
| Methylparaben | 0.30 |
| Polysorbate 20 | 0.25 |
| Disodium EDTA | 0.10 |
| Germall II | 0.10 |
| Total → | 100.00 |

ANHYDROUS SERUM

| INGREDIENT | % w/w |
|---|---|
| Cyclomethicone | 72.40 |
| Gum Mastic | 1.00 |
| Isopropyl Myristate | 5.00 |
| Octyl Palmitate | 3.00 |
| Polyglycerol-6 Dioleate | 5.00 |
| Butylene Glycol | 4.00 |
| Dimethicone, 100 cst | 5.00 |
| Beeswax | 0.30 |
| Propylparaben | 0.20 |
| Fragrance | 0.10 |
| Total → | 100.00 |

-continued

| INGREDIENT | % w/w |
|---|---|
| HYDRO-ALCOHOLIC GEL | |
| DI Water | 52.85 |
| Alcohol SDA40B | 30.00 |
| Butylene Glycol | 5.00 |
| PPG-5-Ceteth 20 | 5.00 |
| Glycerin | 3.00 |
| Carbomer | 1.20 |
| Triethanolamine 99% | 1.20 |
| Gum Mastic | 1.00 |
| Methylparaben | 0.30 |
| Polysorbate 20 | 0.25 |
| Disodium EDTA | 0.10 |
| Germall II | 0.10 |
| Total → | 100.00 |

What is claimed is:

1. An oil-in-water cosmetic skin care emulsion composition consisting essentially of:

(a) about 0.001 wt. % to about 10 wt. % of solubilized gum mastic;

(b) a volatile, water miscible solvent; and (c) a cosmetically acceptable vehicle.

2. The composition of claim 1 comprising about 0.01 wt. % to about 3 wt. % of solubilized gum mastic.

3. A cosmetic skin care method of reducing or preventing oily skin conditions, the method comprising applying to the skin the gum mastic composition of claim 1.

4. A cosmetic skin care method of stimulating collagen synthesis by fibroblasts in the skin, the method comprising applying to the skin the gum mastic composition of claim 1.

5. A cosmetic skin care method of treating aged, photoaged, dry, lined or wrinkled skin, the method comprising the step of applying to the skin the gum mastic composition of claim 1.

6. A cosmetic skin care method of reducing or preventing oily skin conditions as well as treating aged, photoaged, dry, lined or wrinkled skin, the method comprising the step of applying to the skin the gum mastic composition of claim 1.

* * * * *

UNITED STATES PATENT AND TRADEMARK OFFICE
CERTIFICATE OF CORRECTION

PATENT NO.    : 6,623,728 B2                                                           Page 1 of 1
DATED         : September 23, 2003
INVENTOR(S)   : Bijan Harichian, John Steven Bajor and Laura Rose Palanker It is certified that error appears in the above-identified patent and that said Letters Patent is hereby corrected as shown below:

<u>Title page,</u>
Item [75], Inventors, the first named inventor is listed as:
"Bijan Steven Harichian, Warren, NJ" and should be listed as:
-- Bijan Harichian, Warren, NJ --

Signed and Sealed this

Twentieth Day of January, 2004

JON W. DUDAS
*Acting Director of the United States Patent and Trademark Office*